(12) United States Patent
Ruby

(10) Patent No.: US 8,633,324 B2
(45) Date of Patent: Jan. 21, 2014

(54) DENIBULIN DI-HYDROCHLORIDE

(75) Inventor: Kale Ruby, Encinitas, CA (US)

(73) Assignee: Medicinova, Inc., La Jolla, CA (US)

( * ) Notice: Subject to any disclaimer, the term of this patent is extended or adjusted under 35 U.S.C. 154(b) by 0 days.

(21) Appl. No.: 13/560,785

(22) Filed: Jul. 27, 2012

(65) Prior Publication Data
US 2013/0041002 A1 Feb. 14, 2013

Related U.S. Application Data

(60) Provisional application No. 61/457,994, filed on Jul. 29, 2011.

(51) Int. Cl.
A61K 31/4184 (2006.01)
C07D 235/32 (2006.01)

(52) U.S. Cl.
USPC ........................................ 548/309.1; 514/388

(58) Field of Classification Search
USPC ...................................................... 548/309.1
See application file for complete search history.

(56) References Cited

U.S. PATENT DOCUMENTS

| 6,645,950 | B1 | 11/2003 | Davis |
| 7,081,469 | B2 | 7/2006 | Davis |
| 2004/0058972 | A1 | 3/2004 | Davis |
| 2005/0267148 | A1 | 12/2005 | Tsuchiya et al. |
| 2006/0264492 | A1 | 11/2006 | Davis |
| 2008/0032954 | A1 | 2/2008 | Ryan |
| 2009/0131852 | A1 | 5/2009 | Hooi |
| 2010/0226943 | A1 | 9/2010 | Brennan et al. |

FOREIGN PATENT DOCUMENTS

| WO | WO-00/40529 | 7/2000 |
| WO | WO-00/41669 | 7/2000 |
| WO | WO-2005/110426 | 11/2005 |
| WO | WO-2006/076376 | 7/2006 |

OTHER PUBLICATIONS

Baguley et al., "Inhibition of growth of colon 38 adenocarcinoma by vinblastine and cholchicine: evidence for a vascular mechanism," European Journal of Cancer, 1991, vol. 27, 482-487.
Cai, "Small Molecule Vascular Disrupting agents: Potential New Drugs for Cancer Treatment," Recent Patents on Anti-Cancer Drug Discovers, 2007, 2, pp. 79-101, Bentham Science Publishers Ltd.
Chaplin et al., "Antivascular approaches to solid tumour therapy: evaluation of tubulin binding agents," British J. Cancer, 27, 1996, S86-S88.
Dark et al., "Combretastatin A-4, an agent that Displays Potent and Selective Toxicity toward Tumor Vasculature," Cancer Research, 57, 1997, 1829-1834.
Holwell et al., "Anti-Vascular and Anti-Tumor Effects of Combretastatin A1 Prodrug," Pharmacology and Experimental Therapeutics 14, Proceedings of the American Association for Cancer Research, 2000, vol. 41, No. 1363, pp. 214.
Hori et al., "Antitumor effects due to irreversible stoppage of tumor tissue blood flow: evaluation of a novel combretastatin A-4 derivative, AC7700," Japanese Journal of Cancer Res. 1999, vol. 90, pp. 1026-1038.
International Search Report and Written Opinion issued in PCT/US2012/048528 date of mailing Oct. 1, 2012.
Kalaiselvan et al. "Studies on mechanism of enhanced dissolution of albendazole solid dispersions with crystalline carriers", Indian Journal of Pharmaceutical Sciences, 2006, vol. 68, pp. 599-607.
Lee et al., "Colchicine Site Inhibitors of Microtubule Integrity as Vascular Disrupting Agents," Drug Development Research, 2008, 69, 352-358, Wiley-Liss, Inc.
Shi et al., "Preclinical Studies of the Novel Vascular Disrupting Agent MN-029," Anticancer Research, 2005, 25, 3899-3904.
Traynor et al., "A dose escalation, safety, and tolerability study of MN-029 in patients with advanced solid tumors," Invest New Drugs, 2010, 28, pp. 509-515.
Zwi et al., "The morphological effects of anti-tumor agents flavone acetic acid and 5,6-dimethyl xanthenone acetic acid on the colon 38 mouse tumor," Pathology, 1994,vol. 26, pp. 161-169.

Primary Examiner — Laura L. Stockton
(74) Attorney, Agent, or Firm — Gilberto M. Villacorta; Jeffrey R. Lomprey; Foley & Lardner LLP

(57) ABSTRACT

MN-029 di-hydrochloride (MN-029.2HCl, Formula 2) is a potent vascular targeting agent.

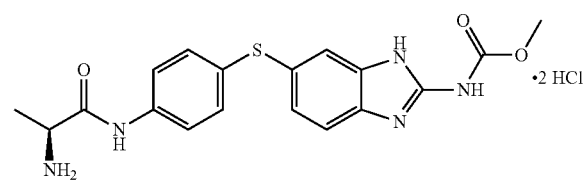

MN-029*2HCl

The present invention focuses on the synthesis and characterization of the di-hydrochloride salt MN-029 and the preparation of pharmaceutically acceptable formulations thereof. Methods are disclosed of using the compound and formulations thereof in the treatment of diseases that rely on the generation of neovasculature by angiogenesis for disease progression.

6 Claims, 13 Drawing Sheets

IRREGULAR CRYSTALLINE PARTICLES UP TO 100μm IN DIAMETER. SIGNIFICANT AGGLOMERATION - TYPICAL AGGLOMERATE DIAMETER OF 500 μm.

POLARIZED LIGHT MICROSCOPY FOR MN - 029*HCl (A063866)

ACICULAR CRYSTALLINE PARTICLES UP TO 40μm IN LENGTH. LOW LEVEL OF AGGLOMERATION - TYPICAL AGGLOMERATE DIAMETER OF 80μm.

POLARIZED LIGHT MICROSCOPY FOR MN - 029*2HCI (A063866)

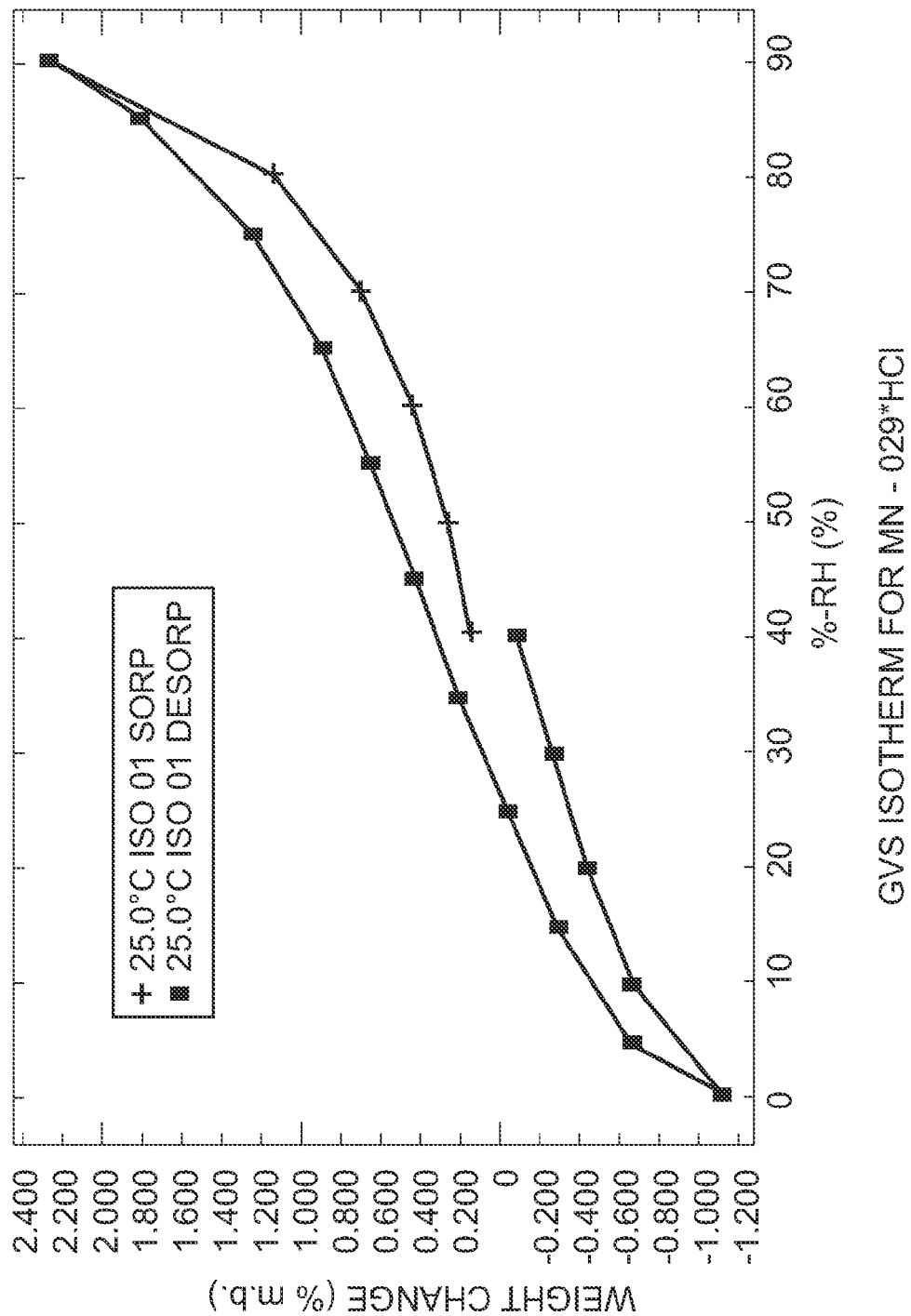

DSC AND TGA THERMOGRAMS FOR MN-029*2HCl

DENIBULIN DI-HYDROCHLORIDE

CROSS-REFERENCE TO RELATED PATENT APPLICATIONS

This application claims priority from U.S. Provisional Application No. 61/457,994, filed Jul. 29, 2011, incorporated herein by reference in its entirety.

BACKGROUND OF THE INVENTION

The present invention relates generally to the field of small molecule therapeutics, specifically, the vascular damaging agent, or vascular disrupting agent carbamic acid N-[6-[[4-[[(2S)-2-amino-1-oxopropyl]amino]phenyl]thio]-1H-benzimidazol-2-yl]-methyl ester di-hydrochloride or denibulin di-hydrochloride (MN-029.2HCl). The formation of neovasculature by angiogenesis is a key pathological step in the development and progress of many diseases, such as cancer, psoriasis, rheumatoid arthritis, macular degeneration and atherosclerotic plaques.

In the cancer field, for example, tumor growth requires the formation of neovasculature to supply critically important nutrients and oxygen to the growing tumor. The formed vascular tissue also serves as a conduit for removing toxic metabolic by-products as well as drug agents from the vicinity of the tumor.

Compounds that damage or prevent neovasculature may find use, therefore, in the treatment of the above mentioned diseases. Several compounds and their pharmaceutically acceptable salts are known to have vascular damaging activity. These agents include, for example, combretastatin A 1 and combretastatin A4 (D. J. Chaplin et al., British J. Cancer 27, S86-S88, 1996), combretastatin A4 phosphate (Dark et al., Cancer Research 57, 1829-1834, 1997), combretastatin A1 phosphate (Holwell et al. Proc. Amer. Assoc. Cancer Res. 41, 1363, 2000), AC7700 (Hori et al. Jpn. J. Cancer Res. 90, 1026-1038, 1999), colchinol derivatives (Davis et al., WO 98/01977 and Davis et al. WO00/40529), benzimidazole derivatives (Davis, WO00/41669), the flavone acetic acids, for example 5,6-dimethylxanthenone acetic acid (Zwi, Pathology, 26, 161-9, 1994) and colchicine (Baguley et al. Eur J Cancer 27, 482-7, 1991).

MN-029 is a known vascular damaging agent that is currently being tested as a candidate therapeutic for treating cancer. The present invention focuses on the discovery of a di-hydrochloride salt form of MN-029, which is useful as a therapeutic agent and exhibits certain advantages over other salt forms of MN-029, as further described in what follows. Pharmaceutically acceptable compositions of the di-hydrochloride salt form of MN-029 are described herein. The present invention also pertains to a method of treating, or the use of the inventive composition in treating the aforementioned diseases by administrating to a subject in need thereof the inventive composition of MN-029 or a combination of the inventive composition with known chemotherapeutics, or in conjunction with radiation and chemo-radiation protocols.

SUMMARY OF THE INVENTION

The present invention is directed to the di-hydrochloride salt of MN-029 as well as its use as a therapeutic. In one embodiment, the invention provides MN-029 di-hydrochloride (MN-029.2HCl) in solid form, which can be characterized by an X-ray powder diffraction (XRPD) trace pattern (or spectrum) having the following peaks expressed in degrees 2-theta (2θ): 15.01, 20.98, 21.49, 22.52, 23.15, 24.27, 25.80 and 26.57. The claimed solid form further exhibits the following peaks in its diffractogram 11.10, 15.9, 18.03, 21.25 and 27.43.

Another embodiment of the invention provides a pharmaceutical composition comprising MN-029 di-hydrochloride along with one or more various pharmaceutically acceptable excipients. In an aspect of this embodiment, the pharmaceutical composition is provided as a lyophilized preparation.

Yet another embodiment of the invention provides a method of treatment comprising the administration of a therapeutically effective amount of MN-029 di-hydrochloride as a vascular targeting agent for treating a cell proliferative disease in a mammal. Examples of cell proliferative diseases, without limitation, include cancer, psoriasis, rheumatoid arthritis, macular degeneration and atherosclerotic plaques.

The present invention also provides a method for reconstituting a lypophilized pharmaceutical preparation comprising the inventive Formula 2 compound, which method comprises adding to the lyophilized pharmaceutical preparation an effective amount of a pharmaceutically acceptable solvent to provide a solution. The solution is suitable for administration to a patient in need of therapy.

DETAILED DESCRIPTION OF THE PREFERRED EMBODIMENTS

Free carbamic acid N-[6-[[4-[[(2S)-2-amino-1-oxopropyl]amino]phenyl]thio]-1H-benzimidazol-2-yl]-methyl ester also known by its trade name denibulin or MN-029, is a commercially available vascular disrupting agent (VDA), whose structure is depicted below in Formula 1.

The structures of MN-029 free base and its di-hydrochloride salt are depicted below.

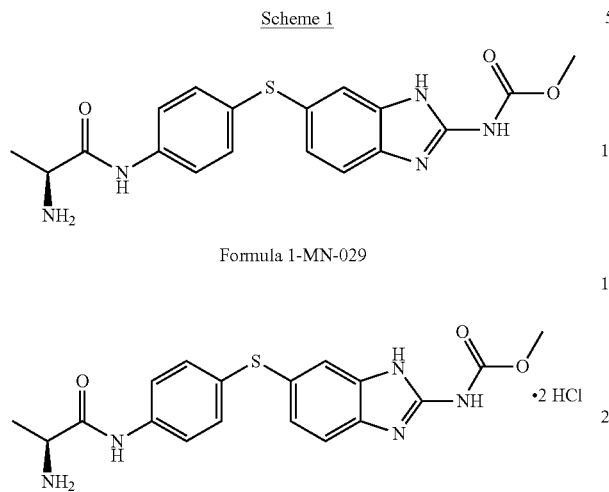

Scheme 1

Formula 1-MN-029

Formula 2-MN-029*2HCl

The free base of MN-029 (Formula 1, Registry No. 284019-34-7), its mono-hydrochloride salt (Registry No. 779356-64-8) and its bis-trifluoroacetate salt (Registry No. 931410-84-3) are known. The di-hydrochloride salt is novel, however. The present invention, therefore, focuses on the preparation, characterization and use of the di-hydrochloride salt form of MN-029 (MN-029.2HCl, Formula 2) for the treatment of diseases rooted in uncontrolled cell proliferation and/or unwanted tissue growth, such as the many types of solid tumors and cancer.

According to one embodiment, therefore, the present invention characterizes MN-029.2HCl, using different analytical methods, including but not limited to proton nuclear magnetic resonance spectroscopy ($^1$H NMR), Fourier transform infra red spectroscopy (FT-IR), optical microscopy, differential scanning calorimetry (DSC), thermogravimetric analysis (TGA) and X-ray powder diffraction (XRPD) pattern. According to an aspect of the present invention, therefore, the inventive MN-029.2HCl salt is characterized by X-ray powder diffraction spectroscopy (XRPD), and expressing the diffracted X-ray peaks characteristic of MN-029.2HCl in terms of the angle of reflection expressed in degrees 2-theta (2θ). As further discussed below, XRPD data was obtained using CuKα$_1$ as the source of X-ray radiation and the data obtained was analyzed and presented using Diffrac Plus EVA software v11.0.0.2.

Table 1, below, provides a list for 2θ peaks that were obtained for the di-hydrochloride salt of MN-29, while Table 2 provides for comparative purposes a peak list of 2θ values for the mono-hydrochloride salt of MN-029.

Figure 1:
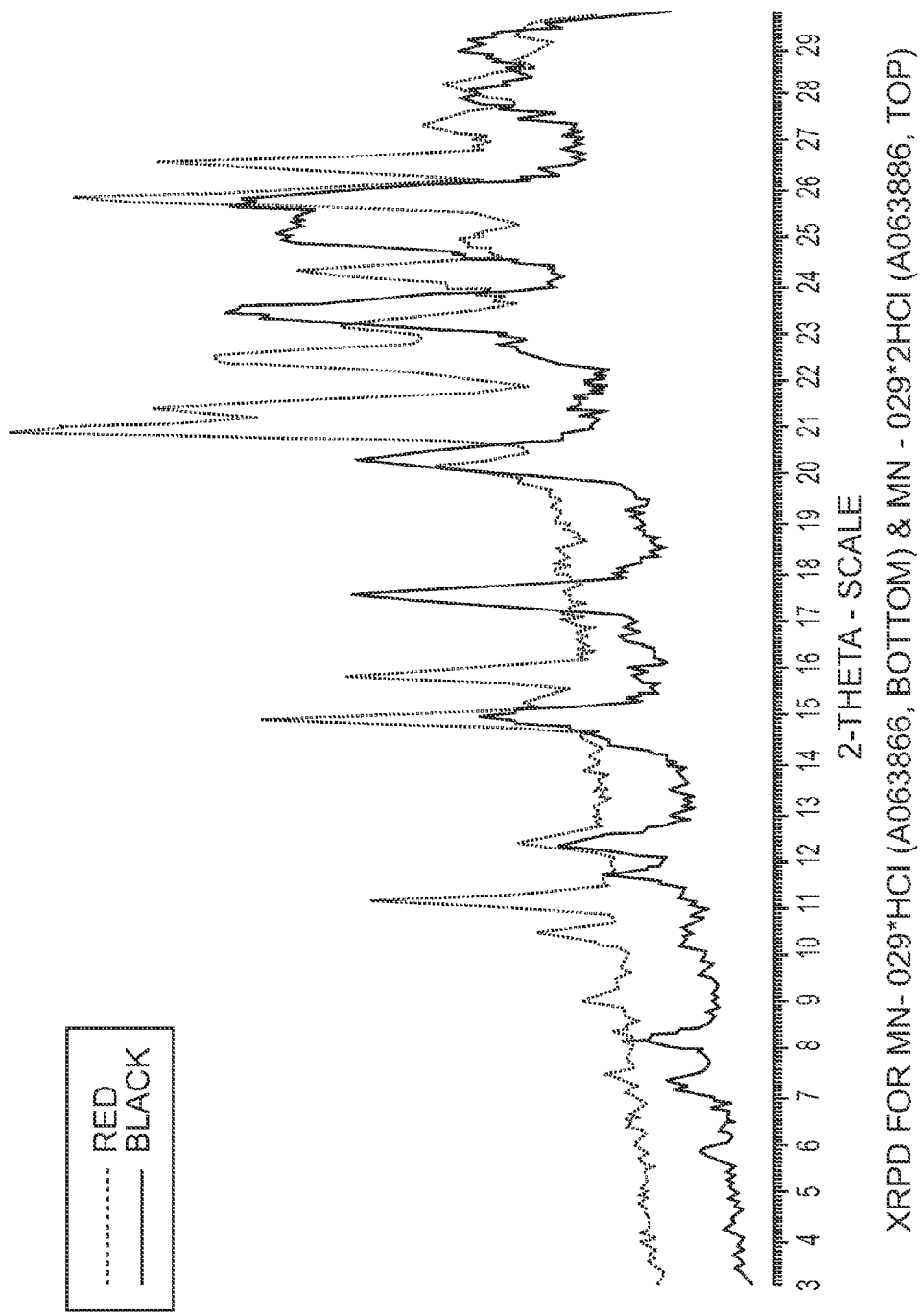
FIG. 1. X-ray powder diffraction pattern of the mono- and di-hydrochloride salt form of MN-029.

Comparing the 2θ values in Tables 1 and 2, it is evident that while the relative intensities of certain peaks may vary, the respective peak positions remain constant and can serve as indicia to distinguish the di-hydrochloride salt of MN-029 from the corresponding mono-hydrochloride salt of MN-029. For instance, the data, in Table 1 indicates that the following 2θ peaks are characteristic of MN-029 di-hydrochloride salt: 11.10, 15.01, 15.9, 18.03, 20.98, 21.25, 21.49, 22.52, 23.15, 24.27, 25.80, 26.57 and 27.43. See, FIG. 1 and Table 1, below.

TABLE 1

| Angle/2θ° | Intensity/% |
|---|---|
| 10.45 | 13.0 |
| 11.10 | 39.6 |
| 12.36 | 20.1 |
| 15.01 | 63.9 |
| 15.33 | 12.9 |
| 15.90 | 45.9 |
| 18.03 | 12.8 |
| 20.21 | 33.3 |
| 20.98 | 86.0 |
| 21.25 | 41.7 |
| 21.49 | 67.1 |
| 22.25 | 27.8 |
| 22.52 | 63.4 |
| 22.83 | 25.8 |
| 23.15 | 45.0 |
| 23.83 | 12.6 |
| 24.27 | 46.2 |
| 24.95 | 18.3 |
| 25.80 | 100.0 |
| 26.57 | 59.2 |
| 27.43 | 29.9 |
| 28.25 | 27.3 |
| 28.72 | 22.7 |
| 29.30 | 20.7 |
| 29.85 | 18.8 |
| 31.62 | 22.6 |
| 32.00 | 29.4 |
| 32.55 | 12.6 |
| 33.05 | 23.7 |
| 33.40 | 15.3 |
| 34.90 | 22.9 |
| 35.46 | 21.8 |
| 35.70 | 16.6 |
| 36.07 | 16.0 |
| 36.82 | 28.0 |
| 37.36 | 25.9 |
| 38.00 | 18.2 |
| 38.93 | 14.0 |
| 40.95 | 11.8 |
| 41.66 | 19.7 |

TABLE 2

| Angle/2θ° | Intensity/% |
|---|---|
| 17.47 | 84.6 |
| 17.89 | 23.6 |
| 20.24 | 53.8 |
| 20.99 | 28.0 |
| 21.51 | 23.3 |
| 22.61 | 40.9 |
| 23.48 | 100.0 |
| 24.28 | 24.9 |
| 24.84 | 58.4 |
| 25.80 | 87.2 |
| 26.58 | 23.7 |
| 28.07 | 47.6 |
| 28.93 | 61.8 |
| 30.83 | 26.6 |
| 31.09 | 31.4 |
| 32.32 | 34.4 |
| 32.60 | 33.5 |
| 33.92 | 28.3 |
| 35.71 | 28.3 |
| 36.74 | 26.9 |
| 37.49 | 23.6 |

Denibulin's activity as a vascular damaging agent makes this compound a candidate therapeutic agent for treating disease conditions that require the development and progression of neovasculature by angiogenesis for the development and progression of disease. In the context of the present invention the terms "vascular disrupting agent," or "vascular damaging agent," or "vascular targeting agent" are being used interchangeably and refer to a compound or its pharmaceutically acceptable salt, solvate, or pro-drug that is capable of damaging, occluding, inhibiting the creation of, or slowing the progression of the vasculature, for example of cancer tumors, and causing central necrosis. Exemplary of such disease states include without limitation cancer, psoriasis, rheumatoid arthritis, macular degeneration and atherosclerotic plaques. Indeed, it has been reported that denibulin can be used as a therapeutic for treating advanced solid tumors.

The therapeutic efficacy of denibulin (MN-029), however, has been hampered in a clinical setting due to the poor water solubility of this compound. The present invention improves aqueous solubility and bioavailability, however, by providing the di-hydrochloride salt of MN-029. To evaluate whether the improved physiological properties of MN-029.2HCl were in fact due to differences in the physicochemical properties of the di-hydrochloride salt in comparison to the known mono-hydrochloride salt of MN-029, the present inventor performed several analytical studies using a variety of analytical methods to evaluate the stability, hygroscopicity, aqueous solubility, and bioavailability of MN-029.2HCl both in crystalline form and in solution.

Table 3 exemplifies the measured physicochemical properties of the di-hydrochloride salt and compares them to the corresponding properties for MN-029 mono-hydrochloride. Without ascribing to any particular theory, however, the present inventor hypothesizes that many of the observed differences in the physicochemical properties of MN-029.2HCl may play a role in enhancing the bioavailability, therapeutic efficacy and kinetics of biodistribution of MN-029.2HCl.

The advantageous nature of the physicochemical properties of the di-hydrochloride salt of MN-029 seems to be borne out, not just in comparison with the mono-hydrochloride salt but also with three other salts that were prepared to determine each salt's potential to be an active pharmaceutical ingredient. These other salt forms were the mesylate, malonate and sulfate salts of denibulin. Each was deemed unsuitable for use in pharmaceutical formulations because of one or more reasons, including instability, hygroscopicity and deliquescence even at moderate humidity. In contrast the di-hydrochloride salt of MN-029 showed greater solubility and stability in a variety of solvents routinely used in pharmaceutical formulations, including without exception, water, buffer (for example citrate buffer), polyethylene glycol (PEG), propylene glycol, ethanol and Tween 80. See FIG. 4.

TABLE 3

| Analysis | | A063866 mono-hydrochloride | A063886 di-hydrochloride |
|---|---|---|---|
| XRPD | | crystalline sample reference diffractogram collected | crystalline sample reference diffractogram collected |
| $^1$H NMR | | consistent with structure | consistent with structure |
| FT-IR | | reference spectrum collected | reference spectrum collected |
| Optical microscopy | | Irregular crystalline particles up to 100 μm in diameter. Significant agglomeration - typical agglomerate diameter of 500 μm. | Acicular crystalline particles up to 40 μm in length. Low level of agglomeration - typical agglomerate diameter of 80 μm. |
| DSC & TGA Hot-stage microscopy | | No melt below gross degradation. Loss of 0.9% w/w unbound solvent | No melt below gross degradation. Loss of 0.4% w/w unbound solvent |
| GVS | Hygroscopicity | Reversible uptake of +2.12% w/w between 40% RH and 90% RH | Reversible uptake of +0.86% w/w between 40% RH and 90% RH |
| | XRPD of residue | No significant difference from input | No significant difference from input |
| Aqueous solubility | pH of saturated solution | 2.37 | 1.03 |
| | Concentration of filtrate (as mg/ml of free base) | 0.63 | 2.1 |
| | XRPD of residue | No significant difference from input | Very similar to XRPD of A063866 |
| Log P | Predicted by ACD | | 1.27 |
| | Predicted by Syracuse | | 2.30 |
| | Measured | | 2.64 |
| LogP$_{ion}$ (cation) | Measured | | 0.93 |
| LogD | Measured | | 2.10 |
| Stoichiometry | | 1:1.03 | 1:1.87 |

As illustrated by Table 3, the di-hydrochloride form of MN-029 forms acicular crystalline particles that are up to 40 μm in length and exhibit a low level of crystalline agglomeration. (See, FIG. 3.) To the extent that any agglomerates are detected at all, such agglomerates have a diameter 80 μm or less. In one embodiment the agglomeration diameter is about 70 μm, about 60 μm, about 50 μm, about 40 μm, about 30 μm, or about 20 μm. Thus, compared to the mono-hydrochloride salt, the di-hydrochloride salt does not exhibit the irregularly shaped crystalline particles (that are up to 100 μm in diameter) of the mono-hydrochloride salt and does not exhibit the significant agglomeration observed for the mono-hydrochloride, which shows agglomerates having diameters of up to about 500 μm. (See, FIG. 2.)

A percent crystallinity of a sample of MN-029 di-hydrochloride according to the present invention, is preferably at least about 90% crystalline, more preferably about 95% crystalline, still more preferably about 99% crystalline, and most preferably about 99% or 100% crystalline.

Figure 2:
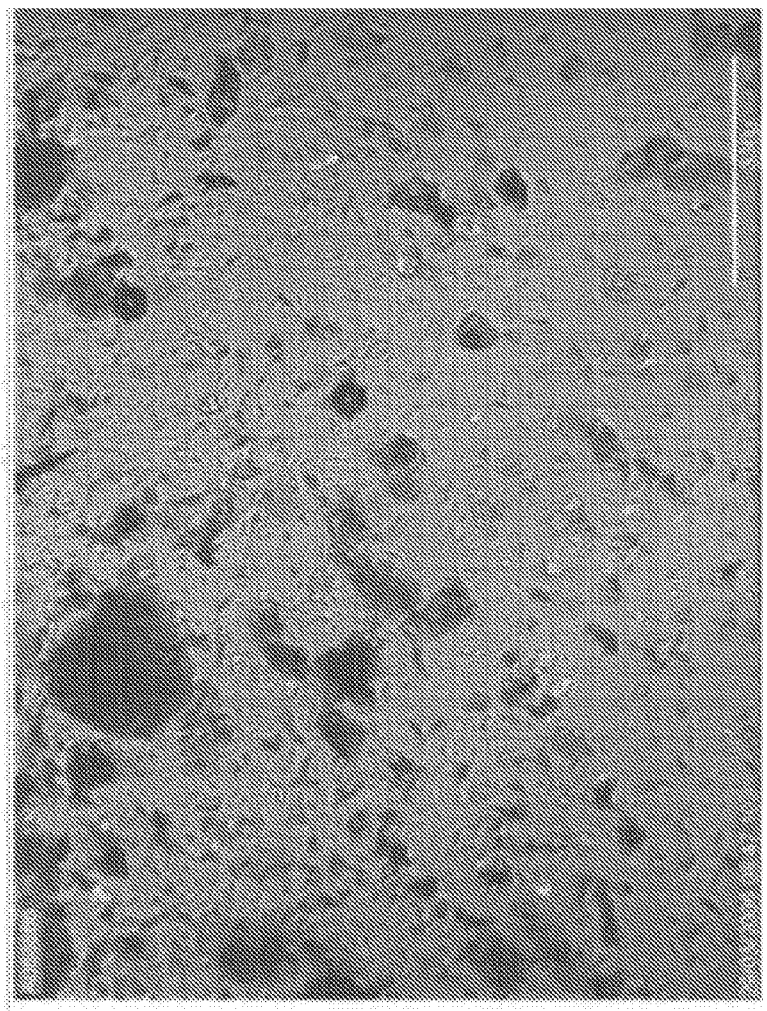
FIG. 2. Polarized light microscopy image of the mono-hydrochloride salt form of MN-029.
Figure 3:
FIG. 3. Polarized light microscopy image of the di-hydrochloride salt form of MN-029.

FIGS. 2 and 3 illustrate polarized light microscopy images of the mono-hydrochloride and di-hydrochloride salts of MN-029, respectively. It is clear from these figures that the mono-hydrochloride salt of MN-029 has irregularly shaped crystalline particles with diameters of a single crystal being up to or in excess of 100 μm. The mono-hydrochloride salt of MN-029 also has a greater propensity to agglomerate. Typically, as observed using polarized light microscopy, the diameter of the crystalline agglomerate is equal to or greater than 500 μm.

These observed differences in the size and form of independent crystals, and differences in the agglomeration behavior of the mono-hydrochloride and di-hydrochloride salts of MN-029 have important physiological and pharmaceutical formulary implications. For instance, higher uniformity of crystal size and shape and the smaller size of MN-029 di-hydrochloride crystals provide a more desirable final formulated medicament with faster, more consistent dissolution kinetics. The improved dissolution kinetics, in turn improves bio-distribution of drug, can increase bioavailability of drug and can improve therapeutic efficacy.

Supporting a role for improved bio-distribution and bioavailability of MN-029.2HCl in vivo are data from an aqueous solubility study that evaluated and compared the pH profile, dissolution properties, hygroscopicity and the hydrophobic:hydrophilic partition coefficient (Log P) of MN-029 di-hydrochloride to corresponding parameters for the mono-hydrochloride salt. Solubility measurements for the hydrochloride salts of MN-029 were obtained in accordance with the procedure outlined below in the characterization section.

Briefly, quantitative high performance liquid chromatography (HPLC) was used to determine the aqueous solubility. X-ray powder diffraction spectrometry was also used to characterize the thermodynamic solubility of the mono-hydrochloride and di-hydrochloride salts of MN-029. After a 24 hours equilibration of each salt form in water at 25° C., the residual solid material was separated from the aqueous solution and the pH of the aqueous sample was measured. The XRPD spectrum of the solid residue obtained from the MN-029 di-hydrochloride vial indicated the solid material to be the mono-hydrochloride salt of MN-029. This result may indicate that under the conditions of the experiment some MN-029 di-hydrochloride may be converted to the corresponding mono-hydrochloride, which being less soluble, does not readily dissolve and remains as a suspended solid even after a period of 24 hours. Table 4 illustrates the data from aqueous solubility studies of the mono-hydrochloride and di-hydrochloride salts of MN-029.

TABLE 4

| Batch | MN-029*HCl | MN-029•2HCl |
|---|---|---|
| Appearance of mixture after equilibration for 24 hours | Pure white suspension | Pure white suspension |
| pH of saturated solution | 2.37 | 1.03 |
| Concentration of filtrate (mg/ml of free base) | 0.63 | 2.1 |
| XRPD of solid residue | No significant difference from input | Very similar to that for MN-029*HCl |

The data in Table 4 illustrate that MN-029.2HCl is more acidic and at least 3-fold more soluble in water than the corresponding mono-hydrochloride salt. It was observed that XRPD analysis of the residue obtained after 24 hour equilibration of the mono-hydrochloride salt of MN-029 in water at 25° C., showed that there was no change in the spectral profile when compared to the XRPD trace of un-equilibrated mono-hydrochloride salt.

Without being held to any particular theory, the present inventor believes that the enhanced solubility of the di-hydrochloride salt is enhanced by the lower pH of the resulting solution. That is, the reduced pH of a solution of the di-hydrochloride of MN-029 improves its aqueous solubility. To test this theory, the present inventor measured the solubility of MN-029 di-hydrochloride in aqueous citric acid and in citrate buffers at different pH values. Two samples of the di-hydrochloride salt in aqueous citric acid were prepared by adding 10 ml of an aqueous citric acid solution to 36.9 mg and 74.5 mg of MN-029 di-hydrochloride salt in a vial. See Table 5.

TABLE 5

| Sample | Weight of Citric Acid | Volume of Water | Weight MN-029•2HCl |
|---|---|---|---|
| 1 | 25.0 mg | 10 ml | 36.9 mg |
| 2 | 47.5 mg | 10 ml | 74.5 mg |

After equilibration with shaking at 25° C. for 12 hours, visual inspection of the solution in each vial indicated a clear colorless solution with no solid residue. Accordingly, the solubility MN-029 di-hydrochloride in aqueous citric acid (4.75 mg/ml) was calculated to exceed 7.54 mg of the di-hydrochloride per milliliter of aqueous citric acid.

To investigate the solubility of MN-029 di-hydrochloride in citrate buffer, the di-hydrochloride salt was added in multiple small portions to 10 milliliters of an aqueous solution of citric acid (3.87 mg/ml). When no more solid dissolved, that is, when saturation was achieved, the solution in the vial was allowed to equilibrate for approximately 24 hours with shaking at 25° C. After equilibration, it was observed that some solid material still remained in the vial indicating that the solution of MN-029 di-hydrochloride was saturated. The pH of the saturated solution was measured prior to filtration of undissolved solid. The filtrate obtained was equally divided into five vials.

To the filtrate in each of the vials was added different volumes of 1M sodium hydroxide so as to increase the pH of the filtrate to a predetermined pH value. See Table 6. It was observed that the addition of base caused solid to precipitate out of solution. The reaction mixture is allowed to equilibrate with shaking at 25° C., following which the solid residue is filtered and the filtrate obtained is analyzed for presence of dissolved compound by HPLC.

TABLE 6

| Sample | pH | Solubility (free base equivalent, mg/ml) |
|---|---|---|
| 1 | 0.96 | 2.9 |
| 2 | 2.03 | 1.6 |
| 3 | 3.23 | 0.039 |
| 4 | 5.57 | <0.001 |
| 5 | 8.55 | Suspension too thick to filter |

Figure 4:
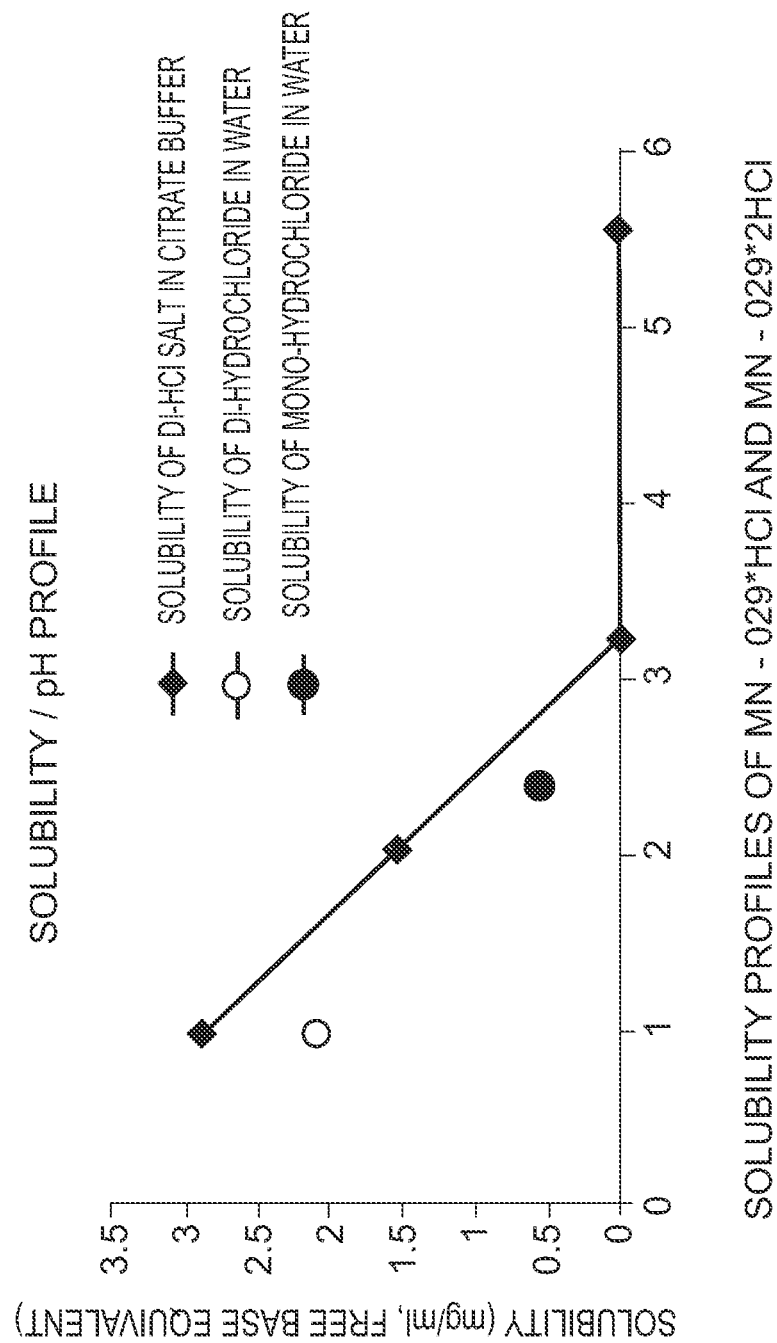
FIG. 4. Graph of solubility of the mono-hydrochloride salt form of MN-029 in water and the di-hydrochloride salt form of MN-029 in water and in a citric acid solution.

Table 6 and FIG. 4 illustrate the results of this study. As shown by the data from HPLC analysis of the filtrates the solubility of MN-029 di-hydrochloride is pH dependent. For instance, maximum solubility is observed at lower pH values with solubility decreasing as the pH of the solution increases. A comparison of the data in Table 6 indicates that at a pH of about 5.5, the di-hydrochloride of MN-029 is approximately 3000-fold less soluble than the solubility of the di-hydrochloride of MN-029 at a pH value of about 1.0.

Moreover, as illustrated by the solubility profiles in FIG. 4, the solubility of MN-029 di-hydrochloride is greater than the corresponding mono-hydrochloride. Moreover, the di-hydrochloride of MN-029, shows greater solubility in aqueous citric acid or citrate buffer than in water.

MN-029 di-hydrochloride can exists in two tautomeric forms involving the benzimidazole ring nitrogen atoms. See Scheme 2.

Scheme 2

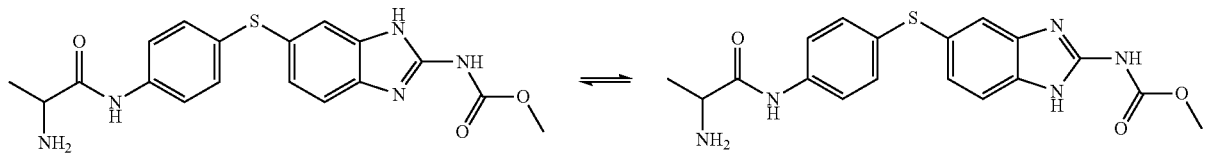

MN-029 has a primary, secondary and tertiary amino group. The pKa's of these amino groups, therefore, should play a role in aqueous solubility, stability and pharmacokinetics. Accordingly, the present inventor compared the predicted pKa's of the alanyl and ring nitrogen atoms to their measured pKa values and unexpectedly found a significant difference between the measured and predicted pKa values for the benzimidazole nitrogen atoms. Thus, for the acidic >N—H group of imidazole, there is approximately a 6-fold difference between the predicted and measured pKa values as shown in Scheme 3. For the more basic ring nitrogen (—N═), however, the difference between observe red and predicted pKa values is 30-fold. That is, the measured value of basicity for the unprotonated ring nitrogen is much lower than the predicted value. In contrast, no significant difference was observed between the predicted and measured pKa values for the alanyl amino group.

TABLE 7

| Humidity Change | Weight change (% w/w) | |
|---|---|---|
| | MN029*HCl | MN029*2HCl |
| 40% RH to 90% RH | +2.12 | +0.86 |
| 90% RH to 0% RH | −3.39 | −1.45 |
| 0% RH to 40% RH | +1.04 | +0.56 |

Figure 6A:
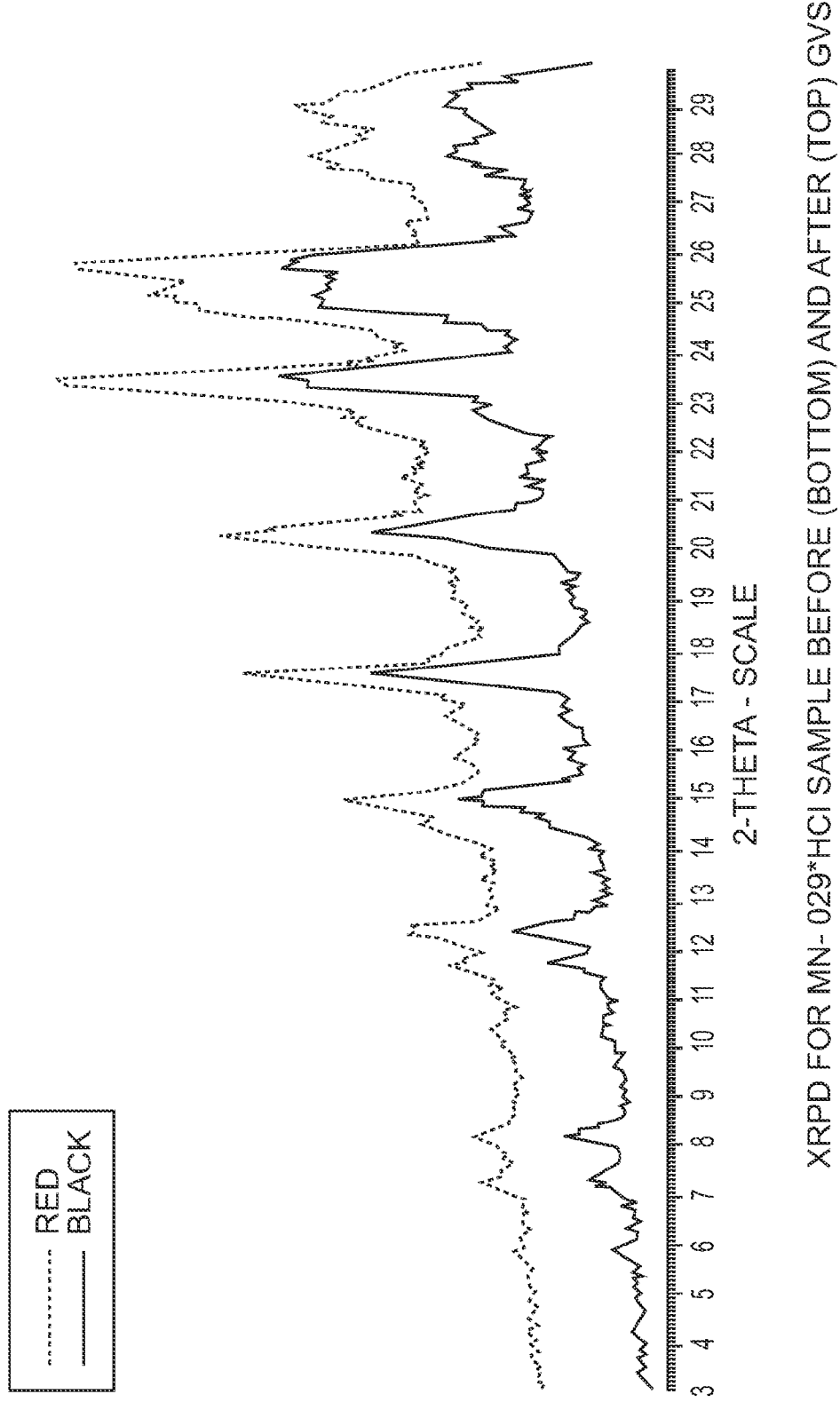
FIG. 6. XRPD Analysis of (A) the mono-hydrochloride of MN-029, and (B) the di-hydrochloride of MN-029 samples subjected to GVS.
Figure 6B:
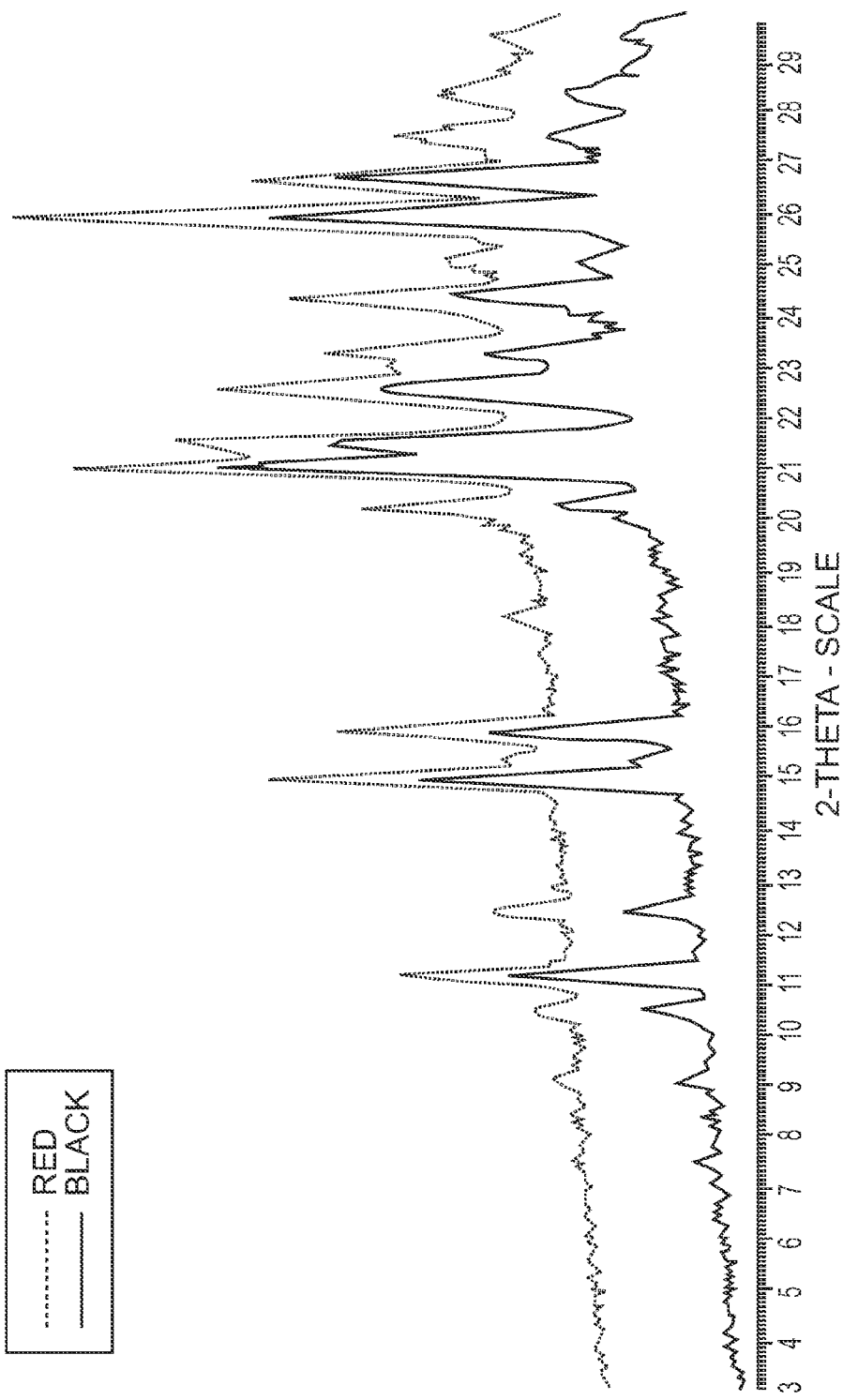

For both the mono-hydrochloride and di-hydrochloride salts, GVS isotherms showed that the moisture adsorbed upon increasing humidity was readily desorbed with little or no hysteresis. Moreover, neither the mono-hydrochloride salt or the di-hydrochloride salt of MN-029 show any significant change in phase as measured by XRPD analysis of samples subjected to GVS analysis (see FIG. 6).

Scheme 3

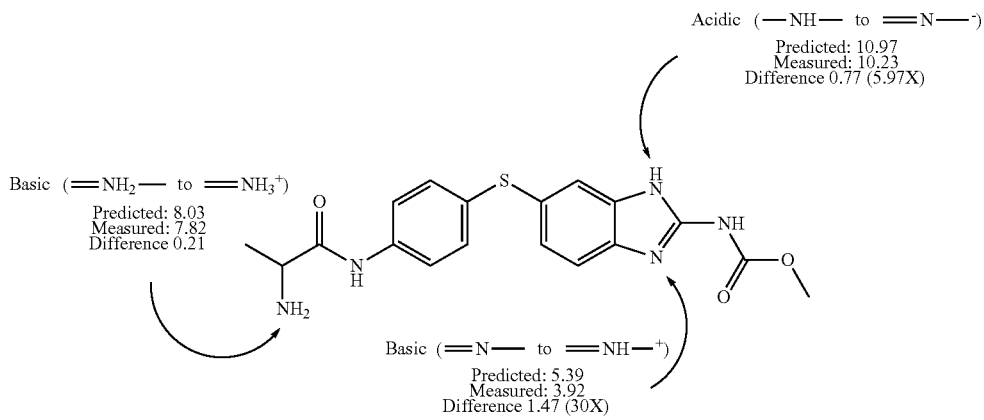

Figure 5B:
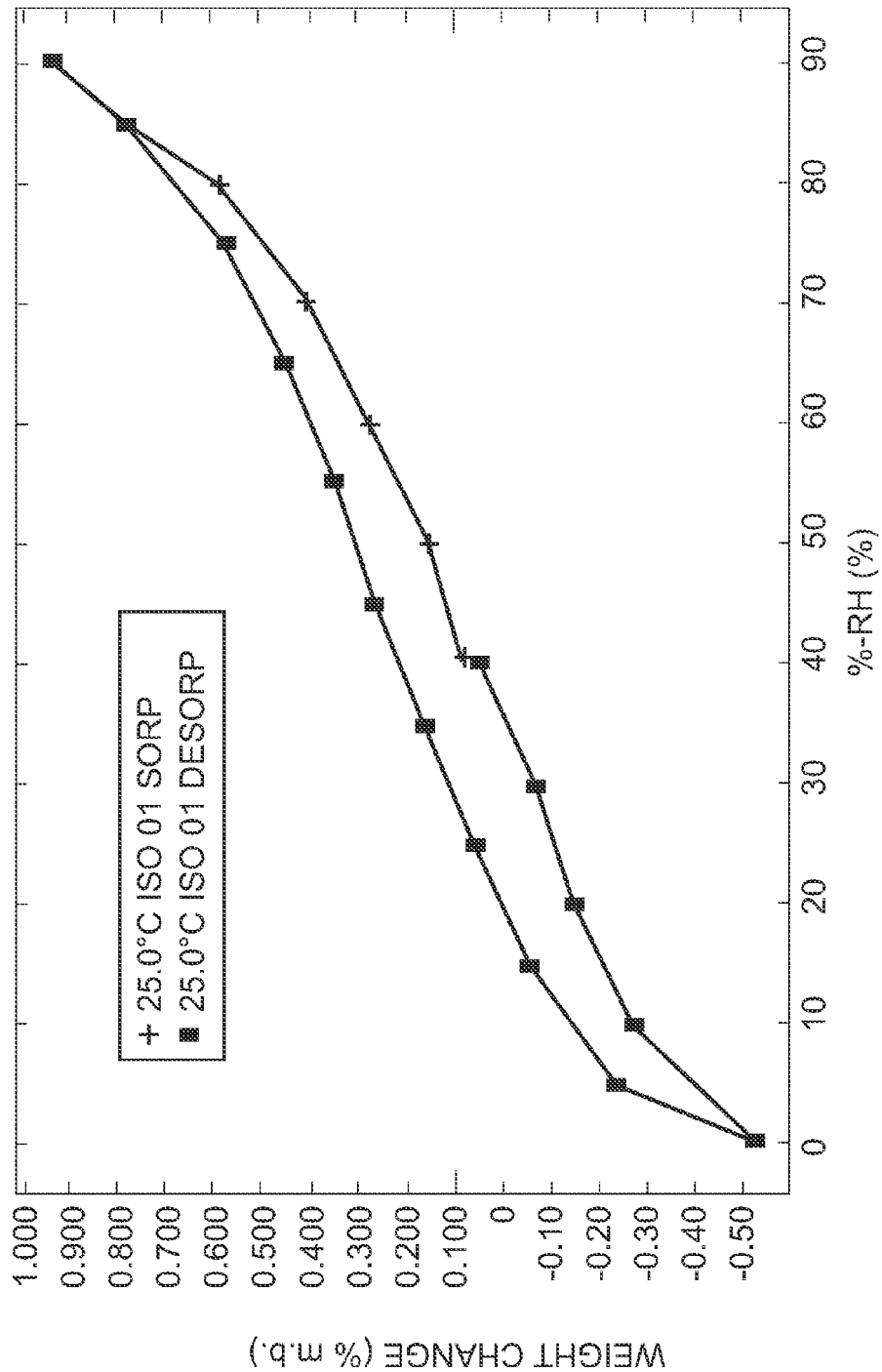
FIG. 5. Gravimetric Vapor Sorption (GVS) isotherm of (A) the mono-hydrochloride of MN-029, and (B) the di-hydrochloride of MN-029.

This difference in basicity may be advantageous. For instance, the di-hydrochloride salt is well-behaved and was found to be at least as stable as the mono-hydrochloride. Gravimetric Vapor Sorption (GVS) isotherms (FIG. 5), moreover, indicate that neither the mono-hydrochloride nor the di-hydrochloride salts of MN-029 are significantly hygroscopic. However, as illustrated by data corresponding to the percent change in weight of sample upon exposure to varying degrees of humidity (Table 7), the di-hydrochloride salt shows a smaller weight change indicating that the di-hydrochloride salt of MN-029 is less hygroscopic than the mono-hydrochloride.

Figure 7A:
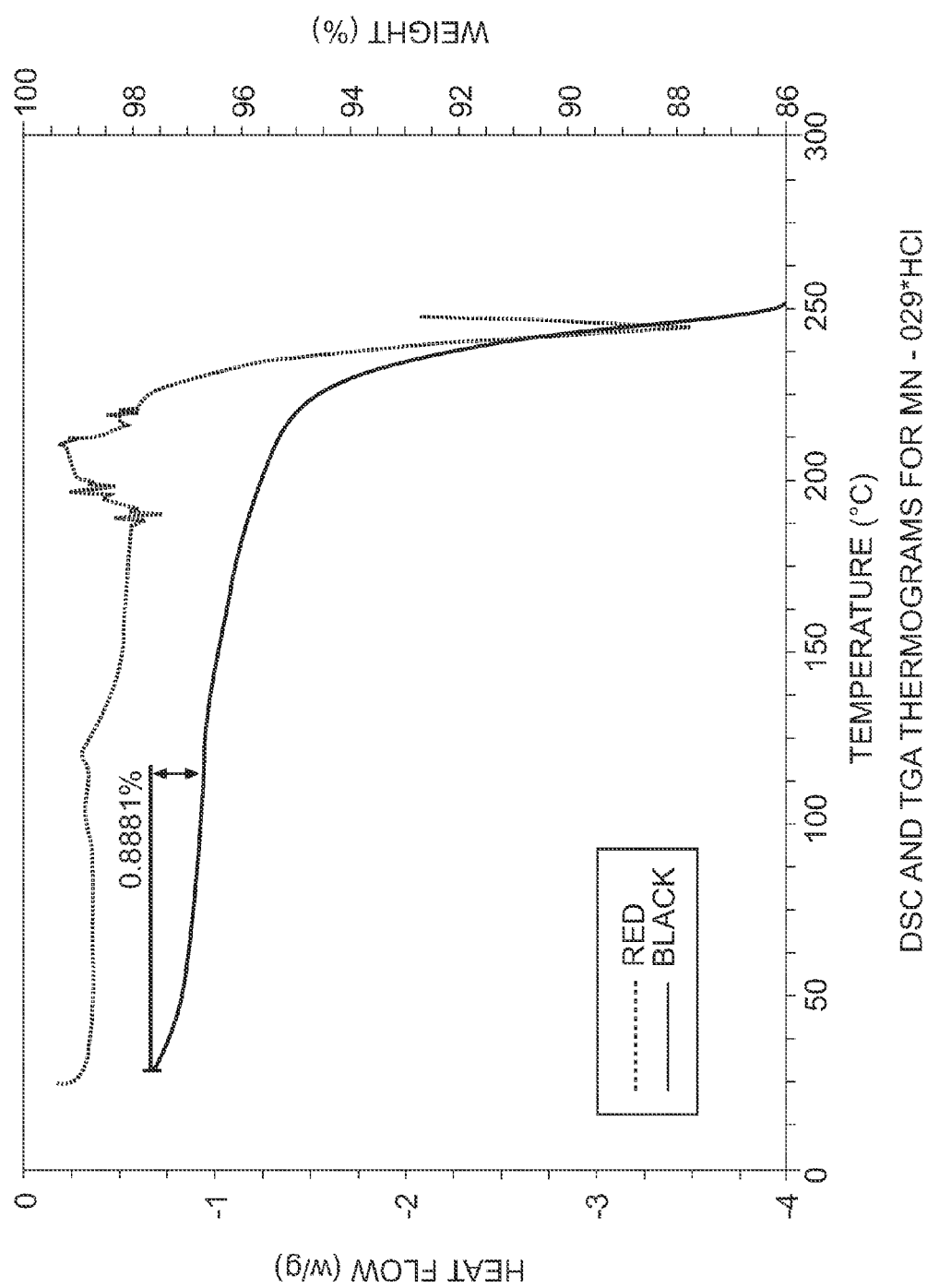
FIG. 7. Differential Scanning calorimetry (DSC) & Thermogravimetric Analysis (TGA) of (A) the mono-hydrochloride of MN-029, and (B) the di-hydrochloride of MN-029.
Figure 7B:
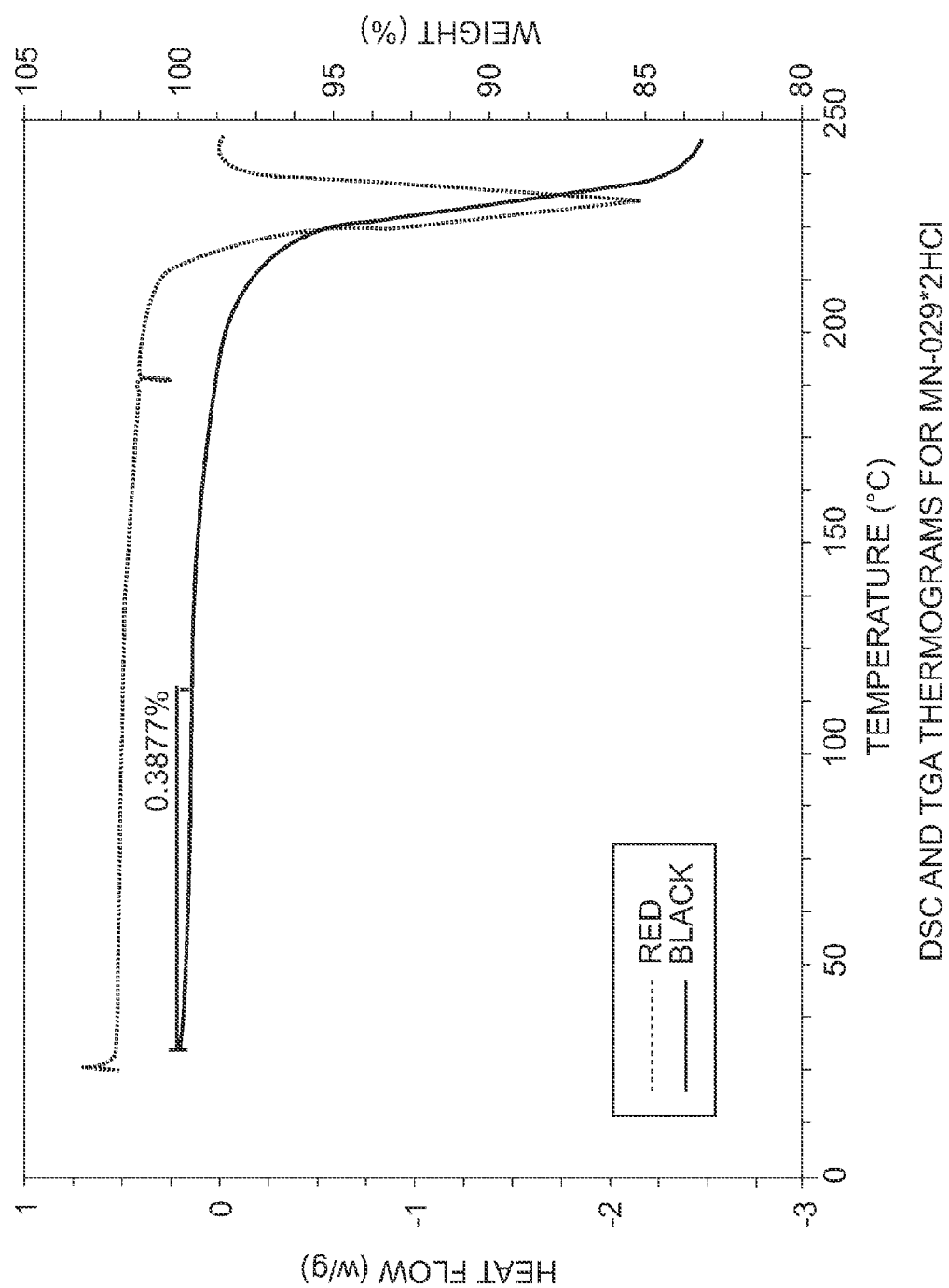

Further support for the greater thermal stability of the di-hydrochloride salt of MN-029 comes from Differential Scanning calorimetry (DSC), and Thermogravimetric Analysis (TGA) of MN-029 mono-hydrochloride and MN-029 di-hydrochloride salts. See, FIG. 7. The endotherms seen in the DSC traces correspond to gross degradation of the sample. There is no suggestion, however, for a change from solid phase to a liquid phase (melting event), for either the mono-hydrochloride or di-hydrochloride salts of MN-029 based on the DSC endotherms. In fact, both the mono-hydrochloride salt of MN-029 and the di-hydrochloride salt of MN-029 degrade at approximately the same temperature, with the mono-hydrochloride salt of MN-029 degrading at a slightly higher temperature than the di-hydrochloride. See, FIG. 7.

Degradation of both samples is accompanied by some loss of unbound solvent when the temperature is raised from an ambient temperature of about 25° C. to approximately 110° C. The mono-hydrochloride looses about 0.9% w/w/ of solvent while the di-hydrochloride salt looses about 0.4% w/w/ of unbound solvent.

A drug's distribution coefficient strongly affects how easily the drug can reach its intended target in the body, how strong an effect it will have once it reaches its target, and how long it will remain in the body in an active form. The partition coefficient (Log P) is one criterion used in medicinal chemistry to assess the "drug-likeness" of a given molecule. The partition coefficient is a ratio of concentrations of un-ionized compound between the two solutions, generally between octanol and water. The log P values is also known as a measure of lipophilicity of a compound.

From a pharmaceutical perspective, log P has a strong influence on ADME properties (Absorption, Distribution, Metabolism, and Excretion) of the drug. Hence, the hydrophobicity of a compound is a major determinant of how "drug-like" it is. For instance, when developing a formulation suitable for oral delivery, it is important to consider if the drug will first pass through lipid bilayers in the intestinal epithelium (a process known as transcellular transport). For efficient transport, the drug must be hydrophobic enough to partition into the lipid bilayer, but not so hydrophobic, that once it is in the bilayer, it will not partition out again. Likewise, hydrophobicity plays a major role in determining where drugs are distributed within the body after absorption and consequently plays an important role in how rapidly a drug is metabolized and excreted.

Most drugs have an ideal log P value and any deviation from this idealized value results in reduced absorption, slow transport of drug to the site of action and consequently, a decrease in biological activity. Table 8, illustrates the predicted and measured values for partition coefficients of MN-029 di-hydrochloride. The data was collected by potentiometric titration using a Sirius GlpKa instrument using three ratios of octanol:ionic-strength adjusted water to generate Log P, Log $P_{ion}$ and Log D values and the raw data was analyzed using Refinement Pro Software V.1.0. The predicted value of Log P was obtained using ACD V. software and Syracuse KOWWIN V.1.67 softwares.

TABLE 8

| | |
|---|---|
| ACD Predicted LogP = | 1.27 |
| Syracuse Predicted LogP = | 2.30 |
| Measured LogP = | 2.64 |
| Measured LogP$_{ion}$(cation) = | 0.93 |
| Measured LogD$_{7.4}$ = | 2.10 |

The stoichiometric ratio of the free base of MN-029 (parent), to mono-hydrochloride salt, or the free base of MN-029 to the di-hydrochloride salt of MN-029 in a crystalline sample was determined by standard potentiometric titration on a Sirius GLpKa instrument. Samples were titrated with approximately 50% methanol co-solvent from about pH 2 to 11 and the data refined using Refinement Pro software version 1.0. For strongly acidic or basic counter ions the acidity or basicity error in the refinement was used to estimate stoichiometry. For acidic or basic counterions having a pKa in the range of 3 to 10, the stoichiometry was calculated from the concentration factor of the counterion relative to the parent.

The stoichiometric ratio of the parent to counterion in the MN-029.2HCl salt is in the range from about 1:1.8 to 1:2.0. In one embodiment the stoichiometric ratio of parent to counterion is 1:1.87. For the purposes of this specification, "parent" refers to MN-029 compound and "counterion" refers to the chloride counterion. Correspondingly, the stoichiometry of parent to counterion for the mono-hydrochloride salt of MN-029 is a 1:1.03, These results conform to predicted value and provide further confirmation with regards to the identity of the mono-hydrochloride and di-hydrochloride salts of MN-029.

Pharmaceutical Compositions and Dosages

The MN-029.2HCl salt of the present invention is thought to be a potent vascular disrupting agent. Accordingly, it is believed to be able to destroy vasculature that has been newly formed while leaving unaffected normal, mature vasculature. Thus, the compound, or compositions of the same, are effective as therapeutics against ailments where neovasculature by angiogenesis is a key pathological step in the development and progress of the disease, such as cancer, psoriasis, rheumatoid arthritis, macular degeneration and atherosclerotic plaques.

Accordingly, in one embodiment the invention provides a pharmaceutical composition comprising the di-hydrochloride salt of MN-029 shown in Scheme 1, and a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, wetting agent, emulsifiers, preservatives, colorants, buffers, flavor imparting agents.

The compounds of the invention may be administered as a sole therapy or in combination with other treatments and therapeutic agents. Co-administration can be carried out by contemporaneous administration of additional therapeutic agents, that is, administering a second medicament before, during, or after the administration of a medicament comprising the compound of the invention. For example, for the treatment of solid tumors the compound of the invention may be administered in combination with radiotherapy or in combination with other anti-tumor substances. Exemplary anti-tumor compounds without limitation include, mitotic inhibitors, for example, vinblastine, paclitaxel and docetaxel; alkylating agents, for example, cisplatin, carboplatin and cyclophosphamide; antimetabolites, for example, 5-fluorouracil, cytosine arabinoside and hydroxyurea; intercalating agents for example adriamycin and bleomycin; enzymes, for example, aspariginase; topoisomerase inhibitors, for example, etoposide, topotecan and irinotecan; thymidylate synthase inhibitors for example raltitrexed; biological response modifiers, for example, interferon; antibodies, for example, edrecolomab and antibodies against the EGFr, HER2 receptor or VEGF receptor: and anti-hormones for example tamoxifen.

For prophylaxis and treatment of disease the compound may be administered as pharmaceutical compositions selected with regard to the intended route of administration and standard pharmaceutical practice. Such pharmaceutical forms may take a form suitable for oral, buccal, nasal, topical, rectal, or parenteral administration and may be prepared by conventional manner using conventional excipients. For example, for parenteral injection (including intravenous, subcutaneous, intramuscular, intravascular or infusion) the composition may take the form of, for example, a sterile solution, suspension or emulsion.

Encompassed within the scope of the invention are pharmaceutical compositions suitable for unit dosage forms that comprise the compound of Formula II its pharmaceutically acceptable stereoisomer, prodrug, solvate, hydrate, or tautomer and a pharmaceutically acceptable carrier.

Inventive compositions suitable for oral use can be prepared according to any method known to the art for the manufacture of pharmaceutical compositions. For instance, liquid formulations of the inventive compounds contain one or more agents selected from the group consisting of sweetening agents, flavoring agents, coloring agents, solubilizing agents and preserving agents in order to provide pharmaceutically elegant and palatable preparations of MN-029.2HCl.

For tablet compositions, the active ingredient in admixture with non-toxic pharmaceutically acceptable excipients is used for the manufacture of tablets. Exemplary of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or coated using any known coating technique to delay disintegration and absorption in the gastrointestinal tract (GI tract) so as to provide a sustained therapeutic action over a desired period of time. For example, a time delayed coating material such as glyceryl monostearate or glyceryl distearate may be employed to coat the tablets.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions the inventive compound is admixed with excipients suitable for maintaining a stable suspension. Examples of such excipients include without limitation sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or the condensation product of an alkylene oxide with fatty acids, for example polyoxyethylene stearate, or the condensation product of ethylene oxide with a long chain aliphatic alcohols, for example heptadecaethyleneoxycetanol. Other exemplary dispersing or wetting agents include the condensation products obtained by reacting ethylene oxide with partial esters of fatty acids and a hexitol or hexitol anhydrides, such as polyoxyethylene sorbitol monooleate, or polyethylene sorbitan monooleate. The aqueous suspensions may also contain one or more preservatives, such as ethyl, or n-propyl p-hydroxybenzoate, one or more coloring agents, one or more flavoring agents, and one or more sweetening agents, such as sucrose or saccharin.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable. The sterile injectable is prepared using a non-toxic parentally acceptable diluent or solvent, for example as a pharmaceutically acceptable buffer, sterile water for injection or other known pharmaceutically acceptable solvents. Among the acceptable vehicles and solvents that may be employed are pharmaceutically acceptable buffer, sterile water for injection, Ringer's solution and isotonic sodium chloride solution. In addition, the injectable can include buffering agents, solubilizing agents and other pharmaceutically acceptable excipients, such as fatty acids, antioxidants, flavoring agents, preservatives and taste masking agents.

Pharmaceutically acceptable carriers suitable for formulating the inventive MN-029 di-hydrochloride include without limitation water, alcohol, for example $C_{2-10}$ aliphatic alcohol or a $C_{3-8}$ cyclic alcohol, gelatin, gum arabic, lactose, starch, magnesium stearate, talc, vegetable oils, polyalkylene-glycols, petroleum jelly, physiologically acceptable buffers, such as, citrate buffer, phosphate buffer, acetate buffer. Formulations of the inventive MN-029 di-hydrochloride can also contain without limitation hydroxypropyl-β-cyclodextrin, polyethyleneglycol-400 (PEG400) and tween 80. Appropriate quantities of one or more carriers in combination with pharmaceutically acceptable adjuvants such as preservatives, stabilizers, wetting agents, and emulsifiers can be used to formulate the inventive MN-029 di-hydrochloride.

According to one embodiment, therefore, a pharmaceutical composition of the inventive MN-029 di-hydrochloride is prepared by reconstituting a lyophilized powder comprising MN-029*2HCl, its tautomer, or a mixture of tautomers and pharmaceutically acceptable excipients with a pharmaceutically acceptable solvent carrier. The amount of solvent added to reconstitute the lyophilized powder must be sufficient to completely dissolve the powder and give a clear solution. Depending on the vehicle used and the concentration of the drug in the formulation, the final volume of the reconstituted preparation can be in the range from about 2 ml to about 10 ml.

According to another embodiment MN-029.2HCl was formulated as an injectable using hydroxypropylbetacyclodextrin as a solubilizing agent, anhydrous citric acid as buffer, hydrochloric acid or sodium hydroxide as pH adjusting agents and sterile water as the solvent. See Table 9. Depending on the vehicle used and the concentration of the drug in the formulation, the final volume of the parenteral formulation can greater than 5 ml. In one embodiment the final volume of the parenteral formulation is in the range from about 1 ml to about 10 ml, for example, the final volume is about 2 ml, about 3 ml, about 4 ml, about 5 ml, about 6 ml, about 7 ml, about 8 ml, about 9 ml or about 10 ml.

TABLE 9

| Ingredient | Function | Amount mg/mL |
| --- | --- | --- |
| MN-209*2HCl | Active ingredient | 6.0[a] |
| Hydroxyproyl-β-cyclodextrin, endotoxin controlled | Solubilizing agent | 150.0 |
| Citric acid anhydrous, USP | Buffer | 3.84 |
| Hydrochloric acid, NF | pH adjustment | — |
| Sodium hydroxide, NF | pH adjustment | — |
| Sterile water for injection, USP | | — |
| Fill volume | | 10.0 mL |

[a]corresponds to 5.0 mg/mL of MN-029 as a free base.

The formulation illustrated above in Table 9, has a pH value of 5.0, a tonicity of 365 mOsm/kg, which is compatible for parenteral delivery, and was stable for a period greater than 2 years at a storage temperature between 2-8° C.

The dose of the compound of the invention required for prophylaxis or treatment of disease will vary depending on the route of administration, the form and severity of the condition and whether the compound is to be delivered alone or in combination with another pharmaceutically active agent. Thus the precise dose will be determined by the administering physician but in general daily doses may be in the range 0.001 to 10 mg/kg preferably 0.1 to 6 mg/kg. In one embodiment, MN-029 di-hydrochloride is injected at a dose of 3 mg/kg, for example, at a dose of 3.5 mg/kg, 4.0 mg/kg, 4.5 mg/kg, 5.0 mg/kg, 5.5 mg/kg, 6 mg/kg, 6.5 mg/kg, 7.0 mg/kg, 7.5 mg/kg, 8.0 mg/kg, 8.5 mg/kg, 9.0 mg/kg, 9.5 mg/kg, 10 mg/kg, 10.5 mg/kg, 11 mg/kg, 11.5 mg/kg, 12 mg/kg, 12.5 mg/kg, 13 mg/kg, 13.5 mg/kg, 14 mg/kg, 14.5 mg/kg, or 15 mg/kg.

The dose administered can also be calculated based on the body surface area (BSA) of a patient. Accordingly, the present invention encompasses injectable formulations that deliver between 10 mg/m$^2$ to 400 mg/m$^2$ free base equivalents of the active pharmaceutical ingredient MN-029. Preferably the pharmaceutical formulation will deliver between 50 to 200 mg/m$^2$ such as, about 100 mg/m$^2$, 120 mg/m$^2$, 140 mg/m$^2$, 146 mg/m$^2$, 180 mg/m$^2$, 200 mg/m$^2$, 220 mg/m$^2$, 240 mg/m$^2$, 260 mg/m$^2$, 280 mg/m$^2$, or 300 mg/m$^2$ of free base equivalents of the active pharmaceutical ingredient MN-029.

The appropriate dose can be administered as a single once-a-day dose or, alternatively, as divided doses throughout the day, optionally taken with food. According to another embodiment the patient or subject undergoing treatment receives a daily dose of MN-029*2HCl as a pharmaceutically acceptable formulation. Alternatively, the appropriate dose is administered as a single dose once-a-week. According to an aspect of this embodiment, once-a-week doses can be administered for 3-5 consecutive weeks followed by a period of no dosing for 1-2 weeks after which once-a-week dosing is continued for another 3-5 consecutive weeks. This dosing schedule is maintained for a duration of time deemed appropriate and necessary by the administering physician.

EXPERIMENTAL

Preparation and Characterization of MN-029.2HCl
A. Synthesis of MN-029 Di-Hydrochloride The MN-029.2HCl salt of the present invention may be prepared by conventional procedures from the free base of MN-029. For example, MN-029 free base is suspended in water or a mixture of water and a suitable organic solvent and the suspension was cooled using an ice bath. To this suspension was added drop-wise two equivalents of concentrated hydrochloric acid. Addition of the acid promotes dissolution as a result of which the solution becomes clear. The reaction mixture is then concentrated in vacuo to precipitate MN-029.2HCl. The solid material obtained was collected by filtration and dried.

B. Characterization of MN-029 Di-Hydrochloride

The solid material was characterized by XRPD. X-Ray Powder Diffraction patterns were collected on a Siemens D5000 diffractometer using CuKu radiation (40 kV, 40 mA), 8-8 goniometer, automatic divergence and receiving slits, a graphite secondary monochromator and a scintillation counter. The instrument is performance was checked using a certified Corundum standard (NIST 1976).

Samples run under ambient conditions were prepared as flat plate specimens using powder as received. Approximately 35 mg of the sample was gently packed into a cavity cut into polished, zero-background (5 I0) silicon wafer. The sample was rotated in its own plane during analysis. The details of the data collection are: range 2° to 42° 2θ; step size 0.05° 2θ; 4 seconds per step. Diffraction data are reported using Cu KUI (Je=1.5406 A), after the Kuz component has been stripped using the instrument evaluation software (EVA). Indexing of powder patterns is carried out by the ITO method using WfN-INDEX, and the raw lattice constants is refined using WIN-METRIC.

In an alternate embodiment, a Bruker AXS/Siemens D5000 Variable Temperature diffractometer (VTX) was used for XRPD analysis under non-ambient conditions. Briefly, Samples run under non-ambient conditions were packed into a stainless steel cavity sample holder equipped with a Pt 100 thermocouple Low temperature data were collected using an Anton Paar TTK450 variable temperature camera attached to the Bruker AXS/Siemens D5000 diffractometer. Instrumental conditions for the low temperature scan were similar to those described for the flat plate samples above. All XRPD analyses were performed using the Diffrac Plus XRD Commander software v2.3.1.

Diffraction data are reported using Cu KUI (Je=1.5406 A), after the Kuz component had been stripped using EVA, the powder patterns were indexed by the ITO method using WIN-INDEX, and the raw lattice constants were refined using WIN-METRIC.

In still another embodiment, X-Ray Powder Diffraction patterns were collected on a Bruker AXS C2 GADDS diffractometer using Cu Ku radiation (40 kV, 40 mA), automated XYZ stage, laser video microscope for auto-sample positioning and a HiStar 2-dimensional area detector. X-ray optics consists of a single Gobel multilayer mirror coupled with a pinhole collimator of 0.3 mm. The beam divergence, i.e., the effective size of the X-ray beam on the sample, was approximately 4 111 m. A 8-8 continuous scan mode was employed with a sample-detector distance of 20 cm which gives an effective 2θ range of 3.2°-29.7°. Typically the sample would be exposed to the X-ray beam for 120 seconds.

Samples run under ambient conditions were prepared as flat plate specimens using powder as received without grinding. Approximately 1-2 mg of the sample was lightly pressed on a glass slide to obtain a flat surface. Samples run under non-ambient conditions were mounted on a silicon wafer with heat conducting compound. The sample was then heated to the appropriate temperature at approximately 20° C. min.$^{-J}$ and subsequently held isothermally for approximately one minute before data collection was initiated.

XRPD data collected in accordance with the parameters set forth above have a margin of error less than ±0.1 °2θ. Other analytical techniques such as $^1$H nuclear magnetic resonance spectroscopy, and Fourier transform infrared spectroscopy were also used to characterize the samples of MN-029.2HCl.

C. Aqueous Solubility Studies

Aqueous solubility was determined my suspending sufficient compound in 0.25 mL of water to give maximum final concentration of greater than or equal to 10 mg per mL of the parent free-form of the compound. The suspension was equilibrated at 25° C. for 24 hours then pH was measured. The suspension was filtered and the filtrate was diluted by a factor of 101. Quantization by HPLC with a reference to a standard solution. Different volumes of the standard, diluted, and undiluted solution were injected and solubility was calculated by integration of the peak found at the same time as the principle peak in the standard solution.

D. Solubility of MN-029 Di-Hydrochloride as a Function of pH

Buffers were prepared to cover a pH range of 2 to 7. Approximately 5 to 10 milligrams of drug was weighed into an HPLC vial to which 1.00 mL of the appropriate buffer was added. The solutions were vortexed briefly and were then shaken for five days on an orbital shaker. The prolonged shaking was carried out because slow equilibration had been observed during the initial formulation studies with different salt forms of MN-029.

Figure 8:
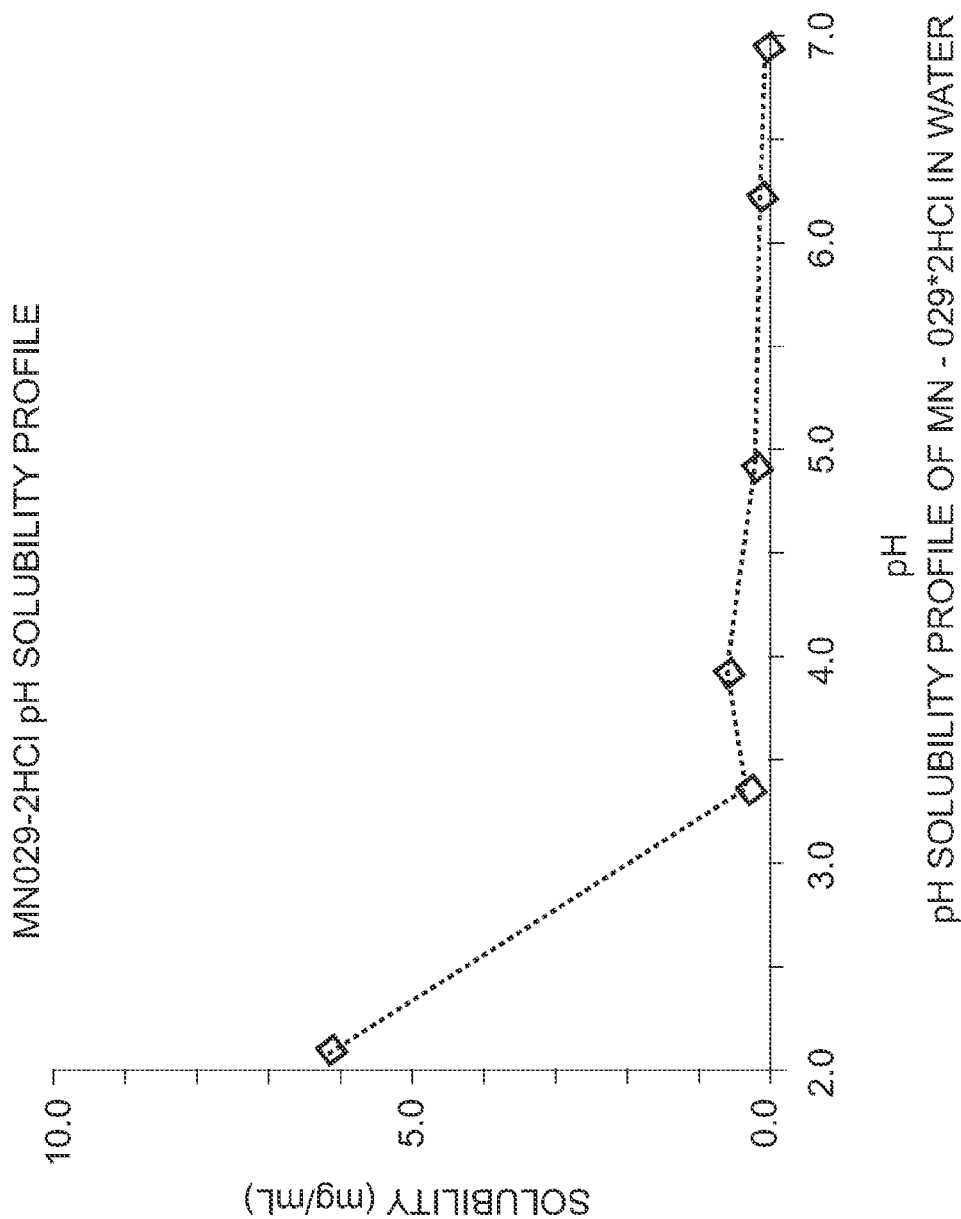
FIG. 8. pH solubility profile of MN-029 di-hydrochloride in water.

Buffers with 15% HPBCD were prepared from the previous buffers. One and a half grams of HPBCD was weighed into each of several 10 mL volumetric flasks. HPBCD was dissolved in and diluted to volume with the appropriate buffer. 15 to 20 milligrams of MN-029 di-hydrochloride was weighed out into an tared HPLC vial. To the di-hydrochloride salt was added 1.00 mL of each buffer and the solution was vortexed briefly to dissolve the salt. The solutions were placed on an orbital shaker for five days. Solubility results are shown in Table 10, and the pH solubility profile for the drug in the absence of HPBCD is shown in FIG. 8.

TABLE 10

| | Without HPBCD | | With 15% HPBCD | |
|---|---|---|---|---|
| Buffer pH | Final pH | MN-029 Solubility (mg/mL) | Final pH | MN-029 Solubility (mg/mL) |
| 2.0 | 2.10 | 6.16 | 2.03 | >20.9 |
| 3.0 | 3.35 | 0.29 | 3.11 | >24.4 |
| 4.0 | 3.92 | 0.56 | 3.98 | >21.5 |
| 5.0 | 4.93 | 0.15 | 5.24 | >23.0 |
| 6.0 | 6.24 | 0.13 | 6.27 | >24.3 |
| 7.0 | 6.96 | 0.026 | 6.90 | >22.7 |

As illustrated by the data in Table 10, the solubility of MN-029 di-hydrochloride in aqueous buffer is about 6 mg/mL at pH 2, but decreases significantly above pH 3. The inclusion of HPBCD improved solubility and negated the solubility dependence on pH. For instance, solubility of MN-029 di-hydrochloride is greater than 20 mg/mL across the tested pH range (pH 2 to pH 6.9), in the presence of 15% HPBCD.

E. Osmolality and pH of MN-029 Di-Hydrochloride

Solutions were prepared by weighing MN-029 di-hydrochloride salt into 10-mL volumetric flasks. The drug was dissolved in water with vortexing, and samples were diluted to volume with water. Solutions of 1, 2, 4, 6 and 8 mg/mL were made according to this procedure. The samples were allowed to sit at room temperature overnight prior to pH and osmolality measurements.

Figure 9:
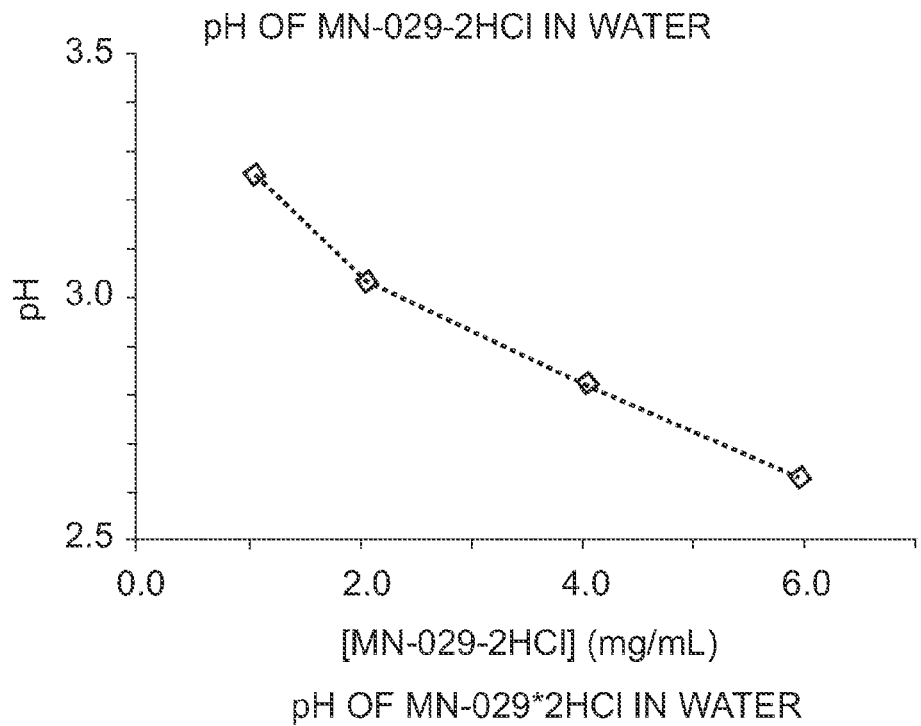
FIG. 9. pH of MN-029 di-hydrochloride in water.
Figure 10:
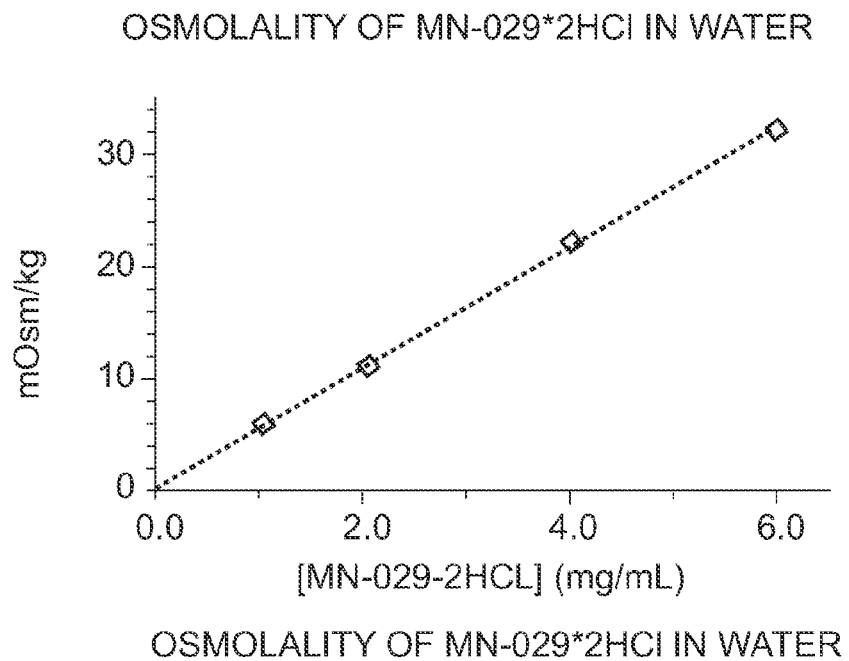
FIG. 10. Osmolality of MN-029 di-hydrochloride in water.

All samples were clear except for the 8 mg/mL solution, which was initially clear but precipitated upon sitting overnight. As shown in Table 10 and in FIGS. 9 and 10, the pH declined in an almost linear fashion with increasing drug concentration while osmolality increased linearly with concentration up to 6 mg/mL.

Figure 11:
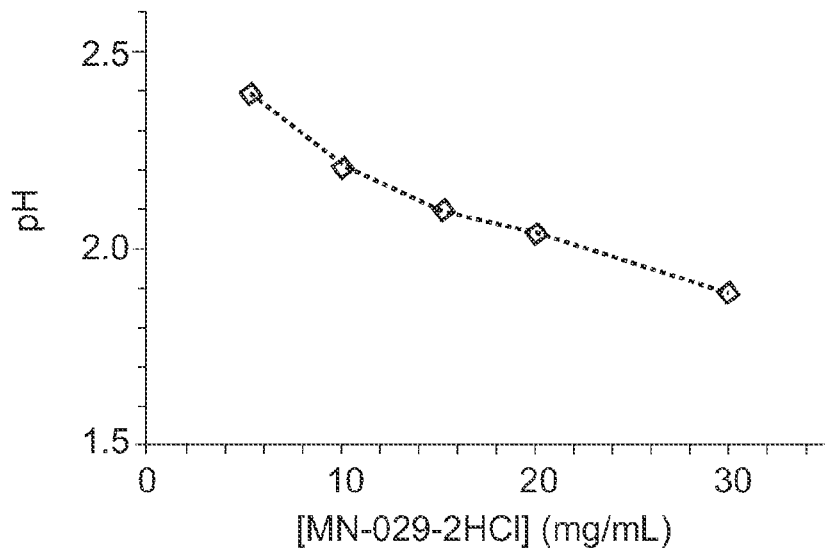
FIG. 11. pH of MN-029 di-hydrochloride in 15% hydroxypropyl-betacyclodextrin.
Figure 12:
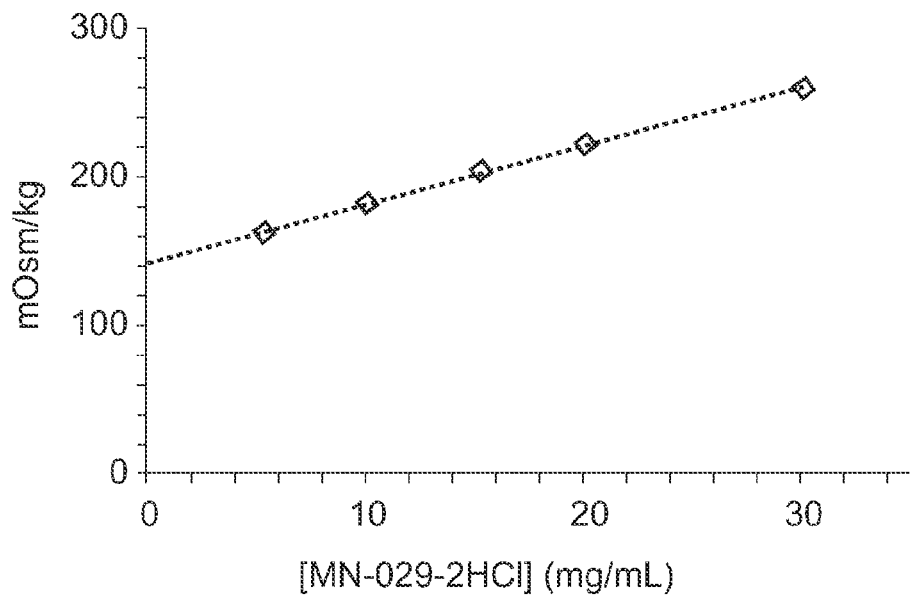
FIG. 12. Osmolality of MN-029 di-hydrochloride in 15% hydroxypropyl-betacyclodextrin.

The pH and osmolality were also measured for solutions of MN-029 di-hydrochloride salt in a 15% solution of hydroxypropyl-β-cyclodextrin (HPBCD). Solutions of 5, 10, 15, 20, and 30 mg/mL were prepared for analysis. The solutions were made by weighing out an appropriate amount of the compound into HPLC vials to which 1.00 mL of 15% HPBCD was added with brief vortexing. Although solutions were clear upon mixing, they were shaken overnight on an orbital shaker to assure equilibration. All solutions remained clear after overnight shaking. HPBCD at a concentration of 15% was sufficient to solubilize MN-029 di-hydrochloride up to a concentration of 30 mg/mL. As shown in Table 11 and in FIGS. 11 and 12, the pH decreased almost linearly with increasing MN-029 di-hydrochloride concentration, while the osmolality increased linearly. The dotted lines on the pH graphs (FIGS. 9 and 11) connect the data points for clarity while the dotted lines on the osmolality graphs (FIGS. 10 and 12) are linear regressions of the data which are extrapolated back to zero drug concentration.

TABLE 11

| In Deionized Water | | | In 15% HPBCD | | |
|---|---|---|---|---|---|
| [MN-029•2HCl] (mg/mL) | pH | Osmolality (mOsm/kg) | [MN-029•2HCl] (mg/mL) | pH | Osmolality (mOsm/kg) |
| 1.05 | 3.25 | 6 | 5.35 | 2.40 | 162 |
| 2.04 | 3.03 | 11 | 10.1 | 2.21 | 182 |
| 4.03 | 2.82 | 22 | 15.3 | 2.10 | 203 |
| 5.96 | 2.63 | 32 | 20.1 | 2.04 | 221 |
| 8.00* | 1.90* | 36* | 30.1 | 1.89 | 259 |

Predicted pKa values were calculated using ACD pKa prediction software v. 9. Actual pKa values were collected on a Sirius GlpKa instrument with a D-PAS attachment. Measurements were made at 25° C. in aqueous solution by UV and in methanol water mixtures by potentiometry. The ionic-strength of the titration media was adjusted with 0.15 M aqueous KCl. The values found in methanol water mixtures were corrected to 0% co-solvent via a Yashuda-Shedlovsky extrapolation. The data were refined using Refinement Pro software v. 1.0. No difference in pKa between the tautomers of MN-029 di-hydrochloride were detected experimentally or theoretically.

What is claimed is:

1. A compound of the Formula 2:

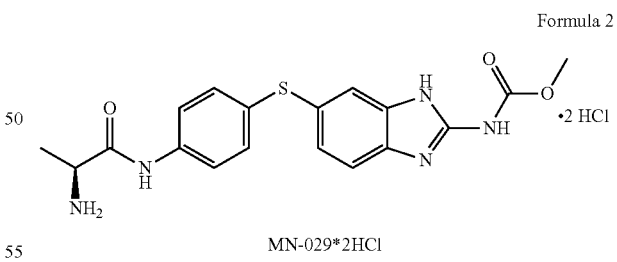

MN-029•2HCl in solid form having an X-ray powder diffraction pattern, obtained using CuKα as the source of radiation, which exhibits the following peaks expressed in degrees 2θ comprising: 15.01, 20.98, 21.49, 22.52, 23.15, 24.27, 25.80 and 26.57.

2. The compound of claim 1, in which the X-ray powder diffraction pattern further exhibits the following peaks expressed in degrees 2θ: 11.10, 15.9, 18.03, 21.25 and 27.43.

3. A pharmaceutical composition comprising a compound of the Formula 2:

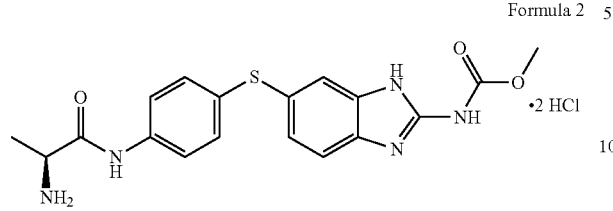

Formula 2

MN-029*2HCl and one or more pharmaceutically acceptable excipients.

4. The pharmaceutically composition of claim 3, which is a lyophilized preparation.

5. A method of treating a cell proliferative disease in a mammal, the method comprising administering an effective amount of denibulin di-hydrochloride to a mammal in need thereof; wherein the cell poliferative disease is selected from the group consisting of solid tumors, psoriasis, rheumatoid arthritis, macular degeneration and atherosclerotic plaques.

6. A method of reconstituting a lyophilized pharmaceutical preparation comprising:

a compound of Formula 2 and one or more pharmaceutically acceptable excipients; and adding to the lyophilized pharmaceutical preparation an effective amount of a pharmaceutically acceptable solvent to provide a solution; wherein the compound of Formula 2 is

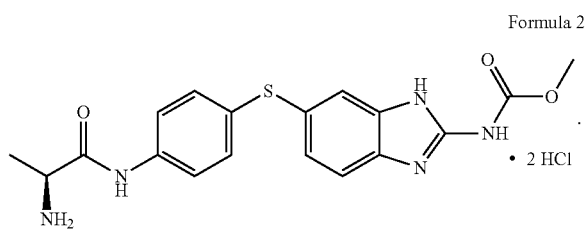

Formula 2

MN-029*2HCl

* * * * *